United States Patent [19]

Ohsumi et al.

[11] Patent Number: 4,599,309
[45] Date of Patent: Jul. 8, 1986

[54] POST CULTIVATION TREATMENT OF YEAST CELLS TO FACILITATE PRODUCT RECOVERY

[75] Inventors: Yoshinori Ohsumi, Chofu; Takanori Sato, Yokohama, both of Japan

[73] Assignee: Nippon Zeon Co., Ltd., Tokyo, Japan

[21] Appl. No.: 560,119

[22] Filed: Dec. 12, 1983

[30] Foreign Application Priority Data

Dec. 14, 1982 [JP] Japan ................................ 57-218766
Dec. 14, 1982 [JP] Japan ................................ 57-218768

[51] Int. Cl.$^4$ ..................... C12P 21/00; C12P 19/38; C12P 19/30; C12P 13/12
[52] U.S. Cl. ........................................ 435/68; 435/87; 435/89; 435/113; 435/255; 435/259; 435/267; 435/270; 435/272
[58] Field of Search ............... 435/68, 161, 90, 171, 435/261, 259, 255, 267, 270, 272, 804, 911, 87, 89, 113, 921, 940, 930; 426/62

[56] References Cited

U.S. PATENT DOCUMENTS

| 1,449,103 | 3/1923 | Hayduck | 426/62 |
| 1,909,011 | 5/1933 | Riley | 426/62 |
| 4,341,802 | 7/1982 | Hopkins | 426/60 |
| 4,414,329 | 11/1983 | Wegner et al. | 435/68 |

OTHER PUBLICATIONS

Khovrychev et al, Chem. Abst., vol. 87, No. 197032n, 1977, "Action of Copper Ions and Unfavorable pH Values of the Medium on the Synthesis of Protein and RNA by Candida utilis cells".

Primary Examiner—Thomas G. Wiseman
Assistant Examiner—R. L. Teskin
Attorney, Agent, or Firm—Sherman and Shalloway

[57] ABSTRACT

Yeast cells containing useful substances accumulated therein are contacted with a divalent copper ion in aqueous suspension, thereby discharging low-molecular-weight compounds in the cytoplasm out of the cells. Useful substances can be efficiently recovered both from the discharged compounds and the remaining cells.

10 Claims, No Drawings

POST CULTIVATION TREATMENT OF YEAST CELLS TO FACILITATE PRODUCT RECOVERY

This invention relates to a method of treating yeast cells in which useful substances are accumulated, and to a method of recovering the useful substances by applying this treating method. More specifically, this invention relates to a method of treating yeast cells, which comprises selectively discharging out of the cells low-molecular-weight compounds present in their cytoplasm, and to a method of efficiently recovering useful substances from the discharged low-molecular-weight compounds or intracellularly accumulated useful substances.

Fermenting methods using yeasts have widely been known, and used, for example, to produce amino acids such as glutamic acid and lysine, vitamins such as vitamin $B_2$ and vitamin $B_{12}$, nucleic acids such as nucleosides, nucleotides, DNA and RNA, and various enzymes.

In these methods, the desired useful substances are generally accumulated intracellularly, and it is necessary to separate the useful substances from the cells by rupturing the cells. Rupturing of the cells is generally carried out by mechanical crushing by a mortar, a homogenizer, a mixer, etc., bacteriolysis by self-digestion, treatment with chemicals such as perchloric acid, sulfuric acid, formic acid, acetic acid, ethyl acetate, acetone, toluene, etc., treatment with a cell wall dissolving enzyme, and so on.

By these general separating methods, the cell walls are destroyed, and all of the substances accumulated in the cells including useful substances are discharged. This causes the defect that subsequent separating and purifying operations become very complex. Furthermore, when chemicals are used, a neutralization step is necessary, or the chemicals cause decomposition or toxification of the useful substances.

If useful substances alone can be selectively separated from the cells by using safe substances or if low-molecular-weight compounds which become impurities can be removed in advance from the cells, the efficiency of subsequent recovery of the useful substances would be greatly increased and the aforesaid problems would be solved altogether.

It is a first object of this invention to provide a method of treating yeast cells by which intracellular components can be separated by a safe and simple operation.

It is a second object of this invention to provide a method of efficiently recovering the desired useful substances from low-molecular-weight compounds present in the cytoplasm of yeast cells by a simple operation.

A third object of this invention is to provide a method of efficiently recovering the desired useful substances from high-molecular-weight compounds present in the cytoplasm of yeast cells or from compounds present in their vacuole.

As a method which can achieve the first object of this invention, there is provided in accordance with this invention a method which comprises contacting yeast cells containing intracellularly accumulated useful substances with a divalent copper ion in aqueous suspension, thereby to discharge low-molecular-weight compounds in the cytoplasm out of the cells.

The yeast cells used in this invention contain, as useful substances, amino acids such as glutamic acid, lysine, aspartic acid, glutamine, homoserine, leucine, methionine, tryptophan and threonine; vitamins such as vitamin $B_1$, vitamin $B_2$, vitamin $B_6$, vitamin $B_{12}$ and pantothenic acid; nucleic acids such as nucleosides, nucleotides, oligonucleotides, DNA and RNA; physiologically active substances such as S-adenosyl-L-methionine (to be referred to as SAM) and glutathione; and proteins such as protease and DNA polymerase. These yeast cells are not particularly limited by the method of production, and any yeast cells which are cultivated in a customary manner can be used as desired.

Specific examples of yeasts are those belonging to genera Saccharomyces, Pichia, Hansenula, Schizosaccharomyces, Saccharomycodes, Hanseniaspora, Torulopsis, Candida, Rhodotorula, and Kluyveromyces. Of these, yeasts of the genera Saccharomyces, Hansenula, Candida, Kluyveromyces and Scizosaccharomyces are preferred. Yeasts of the genus Saccharomyces are especially preferred.

The objects of this invention cannot be achieved when the method of this invention is applied to microorganisms other than yeasts, for example to *Escherichia coli*.

According to the method of this invention, cells are collected from a culture broth in a customary manner, washed as required, and then treated with a divalent copper ion. This treatment can simply be carried out by contacting the cells with a divalent copper ion in aqueous suspension. This treatment results in rapid discharging from the cells of low-molecular-weight compounds having a number average molecular weight of not more than 1,000, particularly not more than 500, such as amino acids, lower peptides, vitamins, nucleosides and nucleotides present in the cytoplasm. On the other hand, high-molecular-weight compounds such as DNA, RNA, proteins and polysaccharides or substances present in the vacuole such as SAM and arginine remain in the cells.

This phenomenon observed in the treatment with a divalent copper ion is unique, and the effect of this invention cannot be achieved by treatment with other divalent metal ions such as divalent Mg, Ca, Sr, Ba, Mn, Fe, Co, Ni, Zn, Sn, Pb and Hg ions.

The conditions for treatment with a divalent copper ion may be chosen according to the purpose of treatment. Usually, an aqueous solution containing a divalent copper ion or a water-soluble divalent copper compound is added to a suspension of the cells in water or a buffer solution, or the cells are directly added to an aqueous solution containing a divalent copper ion; and thereafter, the suspension is left to stand, or stirred. The treatment is carried out usually at a pH of 5 to 7.5, preferably 5.5 to 7. The proportion of the cells in the suspension is usually 1 to 50% by weight, preferably 5 to 30% by weight, as the wet cells. The contacting is carried out usually at 0° to 50° C. for 10 minutes to 3 hours, preferably at 20° to 40° C. for 30 minutes to 2 hours.

Any water-soluble divalent copper compounds may be sources of supplying the divalent copper ion. Specific examples include cupric chloride, cupric bromide, cupric sulfate and cupric acetate. The cupric ion is used in a concentration of usually at least 5$\mu$M, preferably 10 to 50$\mu$M.

As a method which can achieve the second object of this invention, there is provided in accordance with this invention a method which comprises treating yeast cells containing useful low-molecular-weight compounds accumulated in the cytoplasm with a divalent copper ion as described above thereby to discharge the low-molecular-weight compounds out of the cells, and recovering the desired low-molecular-weight useful substances from the discharged materials.

Recovery of useful low-molecular-weight compounds from the discharged materials can be effected by a conventional method, for example by ion-exchange chromatography, gel filtration, electrophoresis, or precipitation with a solvent.

As a method which can achieve the third object of this invention, there is provided in accordance with this invention a method which comprises treating yeast cells containing useful high-molecular-weight compounds accumulated in the cytoplasm or useful compounds accumulated in the vacuole with a divalent copper ion in the manner described above, thereby to discharge low-molecular-weight compounds as impurities in the cytoplasm out of the cells, and thereafter recovering useful substances accumulated in the cells.

Recovery of useful substances from the cells can be effected by a conventional method such as mechanical crushing, or treatment with a cell wall dissolving enzyme. To recover useful substances present in the vacuole, such as SAM, a method of freezing-thawing is advantageously used. This method will be described below in detail.

First, the cells which have been treated with a divalent copper ion are suspended in water after as required they are washed. The amount of water used may be properly chosen. Usually, it is 1 to 100 parts by weight, preferably 3 to 10 parts by weight, per part by weight of the wet cells. If the amount of water is too small, the degree of extraction of useful substances from the cells is not sufficient. If it is too large, the concentration of the useful substances in the aqueous solution is reduced, and much load is exerted on the subsequent purifying and separating step.

Any water which can lead to the freezing of the cells can be used, but from the viewpoint of the degree of extraction, distilled water is preferred. So long as the effect of the present invention is not essentially impaired, a hydrophilic organic solvent may be used together, or water may contain an inorganic salt such as sodium chloride dissolved therein.

In the next place, the suspension is frozen. The freezing temperature and time are not particularly restricted, and any freezing method can be used by which the suspension can be uniformly frozen.

The frozen product is then thawed in a customary manner. The thawing temperature may be properly chosen, and is usually in the range of 0° to 25° C.

The cell residue is removed from the thawed liquid by a conventional method such as centrifugal separation, and then the remaining liquid is treated with an ion exchange resin, activated carbon, a chelate resin, a porous resin, etc. in a customary manner. As a result, the desired useful substances can be isolated.

According to the method of this invention, low-molecular-weight compounds in yeast cells can be separated from other substances therein by a highly safe and simple operation of treating the cells with a cupric ion in a low concentration. As a result, useful substances can be very easily recovered from the separated low-molecular-weight compounds. When the desired useful substances are present in the cells, the purification and separation can also be efficiently carried out since the low-molecular weight compounds as impurities have been previously removed.

The following Examples illustrate the present invention more specifically.

In these examples, all parts are by weight.

EXAMPLE 1

One part (wet weight) of cells obtained by cultivating *Saccharomyces cerevisiae* (X2180-1A, available from Yeast Genetic Stock Center of University of California, Berkeley, U.S.A.) in a YEPD medium (1% yeast extract, 2% bactopeptone, 2% glucose) were suspended in 100 parts of a 100$\mu$M aqueous solution of cupric chloride, and the mixture was stirred slowly at 30° C. After a predetermined period of time, the concentrations of nucleotides, amino acids and proteins present in the aqueous solution were measured, and their proportions per gram of dry cells were calculated on the basis of the measured concentrations. The results are shown in Table 1.

Quantitative analysis of the nucleotides was carried out by measurement of the absorbance of ultraviolet light (260 nm) and high-performance liquid chromatography. Quantitative analysis of the amino acids was carried out by fluorometry using fluorescamine. Quantitative analysis of the proteins was carried out by Lowry's method.

It is seen from the results of Table 1 that by contacting the yeast cells with an aqueous solution containing a cupric ion, the nucleotides and amino acids are rapidly extracted but the proteins are scarcely extracted.

TABLE 1

| Stirring time (min.) | Extracted substances | | |
|---|---|---|---|
| | Nucleotides ($\mu$ moles) | Amino acids ($\mu$ moles) | Proteins (mg) |
| 0 | <1 | <5 | <1 |
| 20 | 20 | 177 | <1 |
| 30 | 21 | 177 | <1 |
| 60 | 23 | 240 | <1 |

EXAMPLE 2

Example 1 was repeated except that the concentration of the aqueous solution containing a cupric ion or the kind of the copper compound was changed as shown in Table 2. The amount of the extracted nucleotides was measured. The results are shown in Table 2.

TABLE 2

| Aqueous solution containing a cupric ion | Amount of nucleotides extracted ($\mu$ moles/g of dry cells) Time (minutes) | | |
|---|---|---|---|
| | 0 | 30 | 60 |
| CuCl$_2$ (10 $\mu$M) | <1 | 2 | 5 |
| CuCl$_2$ (30 $\mu$M) | <1 | 10 | 16 |
| CuCl$_2$ (100 $\mu$M) | <1 | 22 | 24 |
| CuSO$_4$ (100 $\mu$M) | <1 | 23 | 26 |

COMPARATIVE EXAMPLE 1

Example 1 was repeated except that each of the divalent metal compounds indicated in Table 3 was used instead of cupric chloride. The state of extraction of nucleotides was measured, and the results are shown in Table 3. The absorbances at 260 nm show the presence of nucleotides.

TABLE 3

| Divalent metal compound (100 μM) | Absorbance at 260 nm Time (minutes) | | |
|---|---|---|---|
| | 0 | 30 | 60 |
| — | 0.093 | 0.146 | 0.208 |
| MgCl₂ | 0.092 | 0.135 | 0.202 |
| CaCl₂ | 0.117 | 0.136 | 0.200 |
| SrCl₂ | 0.090 | 0.128 | 0.198 |
| BaCl₂ | 0.085 | 0.128 | 0.193 |
| MnCl₂ | 0.085 | 0.131 | 0.196 |
| FeCl₂ | 0.134 | 0.131 | 0.199 |
| CoCl₂ | 0.090 | 0.133 | 0.198 |
| NiCl₂ | 0.088 | 0.134 | 0.198 |
| ZnCl₂ | 0.092 | 0.135 | 0.197 |
| CdCl₂ | 0.091 | 0.130 | 0.198 |
| SnCl₂ | 0.091 | 0.142 | 0.203 |
| Pb(CH₃COO)₂ | 0.091 | 0.131 | 0.209 |
| HgCl₂ | 0.108 | 0.222 | 0.366 |

It is seen from the results obtained that extraction of nucleotides was observed when a mercury ion was used, but with the other metal ions, nucleotides were scarcely extracted.

The data of Example 1 carried out by using cupric chloride correspond to absorbances of 0.108 (for 0 minute), 0.901 (for 30 minutes) and 1.067 (for 60 minutes) when evaluated by the same method as in Table 3. It is understood therefore that the extracting efficiency is much better than that obtained by using a mercury ion.

EXAMPLE 3

Example 1 was repeated except that cells obtained from each of the yeasts indicated in Table 4 were used instead of the cells used in Example 1. The amounts of nucleotides and amino acids extracted were measured, and their proportions per gram of dry cells were calculated. The results are shown in Table 4.

TABLE 4

| | Nucleotides (μ moles) | | | Amino acids (μ moles) | | |
|---|---|---|---|---|---|---|
| | Time (minutes) | | | | | |
| Yeast strain | 0 | 30 | 60 | 0 | 30 | 60 |
| *Hansenula anomala* (IAM 12194 *1) | <1 | 15 | 19 | 10 | 44 | 47 |
| *Candida albicans* (IAM 4966 *2) | <1 | 21 | 24 | 8 | 55 | 58 |
| *Kluyeromyces fragilis* (IAM 12237 *3) | <1 | 45 | 46 | 6 | 60 | 67 |

*1: corresponding to IFO 070 and ATCC 2149
*2: corresponding to IFO 0197
*3: corresponding to IFO 0541

EXAMPLE 4

Five hundred parts of the same cells as used in Example 1 were suspended in 10,000 parts of a 500μM aqueous solution of cupric chloride, and the suspension was stirred at 30° C. for 30 minutes. Then, the cells were removed. The amount of nicotinamide adenine dinucleotide (NAD) contained in the recovered extract was found to be 0.212 part when determined by an enzymatic method using alcohol dehydrogenase.

The extract was passed through a formic acidtype strongly acidic ion exchange resin (Dowex 1X08 made by Rohm & Haas Co.) to cause adsorption of NAD. The resin was then washed with water until the absorbance of the effluent at 260 nm reached less than 0.1. Then, NAD was eluted using an aqueous mixed solution of formic acid (4M) and ammonium formate (0.2M). The NAD eluate thus obtained was purified by sublimation and lyophilization to give 0.170 part of NAD.

EXAMPLE 5

In the same way as in Example 1, the suspension was stirred for 30 minutes. The amount of NAD in the extract was measured, and found to be 3.2μ moles per gram of dry cells. The relative purity of NAD in the substances showing $OD_{260}$ was 15.4%.

COMPARATIVE EXAMPLE 2

One part of the same cells as used in Example 1 was suspended in 100 parts of 1.5N perchloric acid, and the suspension was shaken at room temperature for 1 hour and neutralized with potassium bicarbonate. The resulting precipitate of potassium perchlorate was removed, and the amount of NAD in the extract was measured. It was 5.0μ moles per gram of dry cells, and its relative purity in the substances showing $OD_{260}$ was 2.2%.

EXAMPLE 6

Ten parts (wet weight) of cells containing SAM which were obtained by cultivating *Saccharomyces cerevisiae* (IFO 2044) in the culture medium of F. Schlenk, et al. [Journal of Biological Chemistry, vol. 229, page 1037 (1957)] were washed twice with distilled water, and suspended in 100 parts of tris(hydroxymethyl)aminoethane-2-[N-morpholino]ethanesulfonate buffer adjusted to pH 6.4 (concentration of the buffer 10 mM).

Then, cupric chloride was added to a concentration of 100μM. The mixture was slowly stirred at 30° C. for 1 hour to discharge low-molecular-weight impurities out of the cells. The cells were collected, washed with twice with water, and suspended in 50 parts of distilled water. The suspension was left to stand at −20° C. for 5 hours to freeze it, and then heated indirectly with water at 20° C. to melt it. The insoluble materials were removed from the suspension by centrifugal separation, and the content and purity of SAM contained in the supernatant liquid were measured. The SAM content was 1.70 parts, and its relative purity was 90.9%.

The purity of SAM was determined by the following procedure.

A part of the supernatant liquid was sampled, and developed by two-dimensional paper chromatography. A spot ascribable to SAM was detected, and the concentration of SAM in the sample liquid was detected by an ultraviolet detector. The $OD_{260}$ of the sample liquid was measured. The purity of SAM was calculated in accordance with the following equation.

$$\text{Purity of } SAM = \frac{SAM\ OD_{260}}{OD_{260}} \times 100$$

COMPARATIVE EXAMPLE 3

Ten parts (wet weight) of the same SAM-containing cells as used in Example 6 were suspended in about 50 parts of 1.5N perchloric acid, and the supension was subjected to shaking extraction at room temperature for 1 hour. The cell residue was removed by centrifugal separation. The extract was adjusted to pH 5.0 with potassium bicarbonate. The resulting precipitate of potassium perchlorate was removed by suction filtration, and the content and relative purity of SAM were measured by the same method as in Example 6. The SAM content was 1.73 parts, and its relative purity was 15.6%.

What is claimed is:

1. A method of treating cells of a yeast containing useful substances accumulated therein, which comprises contacting said yeast cells, after cultivation, with a divalent copper ion in an aqueous suspension at a divalent copper ion concentration in the suspension of at least 5μM and at a pH of 5 to 7.5 and a temperature of 0° to 50° C. for 10 minutes to 3 hours thereby to selectively discharge low-molecular-weight compounds having a number average molecular weight of not more than 1000 present in the cytoplasm out of the cells and thereafter recovering the discharged low molecular weight compounds from the treated yeast cells.

2. The method of claim 1 wherein said yeast is a yeast belonging to the genus Saccharomyces, Hansenula, Candida, Kluyveromyces or Schizosaccharomyces.

3. A method of treating cells of a yeast containing useful substances of low-molecular weight having a number average molecular weight of not more than 1000, which comprises contacting said yeast cells, after cultivation, with a divalent copper ion in an aqueous suspension at a pH of 5 to 7.5, a temperature of 0° to 50° C. for 10 minutes to 3 hours and a divalent copper ion concentration in the suspension of at least 5μM thereby to selectively discharge said low-molecular weight compounds present in the cytoplasm out of the cells, and thereafter recovering useful low-molecular-weight substances from the discharged compounds.

4. The method of claim 3 wherein the low-molecular-weight compounds are amino acids, lower peptides, vitamins, nucleosides, or nucleotides.

5. The method of claim 3 wherein the yeast is a yeast belonging to the genus Saccharomyces, Hansenula, Candida, Kluyveromyces or Schizosaccharomyces.

6. A method of treating cells of a yeast containing useful high-molecular-weight substances having a number average molecular weight of more than 1000 accumulated therein, which comprises contacting said yeast cells, after cultivation, with a divalent copper ion in an aqueous suspension at a pH of 5 to 7.5, a temperature of 0° to 50° C. for 10 minutes to 3 hours and a divalent copper ion concentration in the suspension of at least 5μM thereby to selectively discharge low-molecular-weight compounds having number average molecular weight of not more than 1000 present in the cytoplasm out of the cells, and thereafter, recovering said useful high-molecular-weight substances accumulated in the cells.

7. The method of claim 6 wherein the useful substances are high-molecular-weight compounds present in the cytoplasm, or compounds present in the vacuole.

8. The method of claim 7 wherein the compound present in the vacuole is S-adenosyl-L-methionine.

9. The method of claim 8 wherein S-adenosyl-L-methionine is recovered by freezing and thawing.

10. The method of claim 6 wherein the yeast is a yeast belonging to the genus Saccharomyces, Hansenula, Candida, Kluyveromyces or Schizosaccharomyces.

* * * * *